United States Patent [19]

Crenshaw et al.

[11] Patent Number: 4,595,758

[45] Date of Patent: Jun. 17, 1986

[54] ETHANEDIIMIDAMIDE INTERMEDIATES

[75] Inventors: Ronnie R. Crenshaw, Dewitt; Aldo A. Algieri, Fayetteville, both of

[73] Assignee: Bristol-Myers Company, New York, N.Y.

[21] Appl. No.: 677,614

[22] Filed: Dec. 3, 1984

Related U.S. Application Data

[60] Division of Ser. No. 600,864, Apr. 16, 1984, Pat. No. 4,577,366, which is a division of Ser. No. 473,791, Mar. 16, 1983, Pat. No. 4,528,377, which is a continuation-in-part of Ser. No. 363,207, Mar. 29, 1982, abandoned.

[51] Int. Cl.$^4$ ............................................. C07D 409/12
[52] U.S. Cl. ........................................ 546/212; 346/193; 346/208; 346/214; 346/256; 546/284; 546/285; 549/59; 549/74; 549/75; 549/491; 544/60; 544/124; 544/146; 544/152; 544/360; 544/379; 548/517; 548/518; 548/527
[58] Field of Search .................. 549/59, 74, 75, 491; 344/60, 124, 146, 152, 360, 379; 546/193, 208, 212, 214, 256, 285, 284; 548/517, 518, 527

[56] References Cited

U.S. PATENT DOCUMENTS 4,440,933  4/1984  Montzka ............................. 546/193

Primary Examiner—Robert T. Bond
Attorney, Agent, or Firm—Richard R. Lloyd

[57] ABSTRACT

Histamine $H_2$-receptor antagonists of the formula

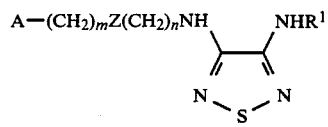

wherein A, m, Z, n and $R^1$ are as defined herein, and their nontoxic pharmaceutically acceptable salts, hydrates and solvates are novel anti-ulcer agents which are prepared by ring closure of a substituted ethanediimidamide of the formula

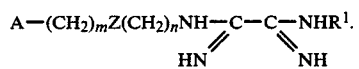

6 Claims, No Drawings 4,595,758

ETHANEDIIMIDAMIDE INTERMEDIATES

CROSS-REFERENCE TO RELATED APPLICATIONS

This application is a divisional of our prior, co-pending application Ser. No. 600,864, filed Apr. 16, 1984, (now U.S. Pat. No. 4,517,366,) which is a divisional of our prior, co-pending application Ser. No. 473,791, filed Mar. 16, 1983, (now U.S. Pat. No. 4,528,377), which is a continuation-in-part of our prior, application Ser. No. 363,207, filed Mar. 29, 1982 (now abandoned).

SUMMARY OF THE INVENTION

Certain 3-(amino or substituted amino)-4-(substituted amino)-1,2,5-thiadiazoles having the formula

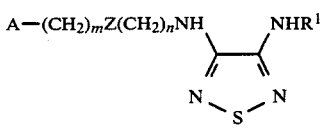

wherein A, m, Z, n and $R^1$ are as defined below, and their nontoxic pharmaceutically acceptable salts, hydrates and solvates, are potent histamine $H_2$-receptor antagonists which inhibit gastric acid secretion and are useful in the treatment of peptic ulcers and other pathological hypersecretory conditions. The compounds are prepared by ring closure of the correspondingly substituted ethanediimidamide of the formula

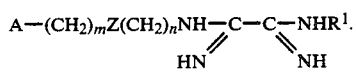

BACKGROUND AND PRIOR ART

Our U.S. Pat. No. 4,374,248, issued Feb. 15, 1983, discloses 3,4-disubstituted-1,2,5-thiadiazole 1-oxides and 1,1-dioxides having the formula

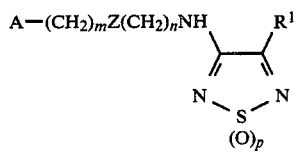

and processes for their preparation, wherein the variables A, m, Z, n and $R^1$ are similar to the corresponding substituents of the compounds disclosed and claimed herein. However, the compounds disclosed therein are 1-oxides or 1,1-dioxides (p is 1 or 2), and the compounds of the present invention cannot be prepared by any of the processes described therein for the preparation of the prior art compounds.

European Patent Application No. 40,696 published Dec. 2, 1981 discloses inter alia 3,4-disubstituted-1,2,5-thiadiazole 1-oxides and 1,1-dioxides having the formula

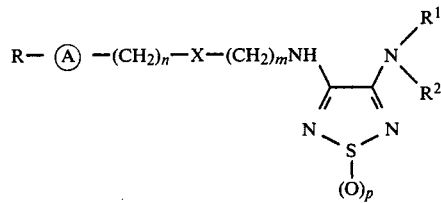

and processes for their preparation, wherein the variables R, Ⓐ, n, X, m, $R^1$ and $R^2$ are similar to the corresponding substituents of the compounds disclosed and claimed herein. However, the compounds disclosed therein also are 1-oxides or 1,1-dioxides (p is 1 or 2) and the compounds of the present invention cannot be prepared by any of the processes described therein for the preparation of the prior art compounds.

In the two publications cited above, each of the processes described for preparation of the prior art compounds involves the use (as a starting material or intermediate) of a 1,2,5-thiadiazole 1-oxide or 1,1-dioxide having either amino groups or suitable "leaving groups" on the 3- and 4-positions. The desired substituents on the 3- and 4-positions are then obtained by substitution on the amino groups or by replacement of the "leaving groups". We have made extensive attempts to prepare the compounds of the present invention by similar procedures, i.e. by utilizing 1,2,5-thiadiazole having amino groups or suitable "leaving groups" on the 3- and 4-positions as starting materials or intermediates. Although numerous variations were tried, along with varying reaction conditions, we were not able to isolate the compounds of this invention by that route.

We have now found that the compounds of the present invention may be prepared by ring closure of the correspondingly substituted ethanediimidamide of the formula

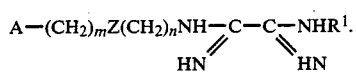

Intermediate II, itself, may be prepared by various procedures.

COMPLETE DESCRIPTION methods;

This invention relates to histamine $H_2$-receptor antagonists of the formula

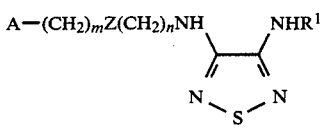

wherein $R^1$ is hydrogen, (lower)alkyl, 2-fluoroethyl, 2,2,2-trifluoroethyl, allyl, propargyl,

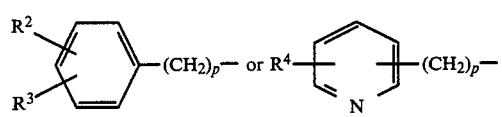

in which p is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;

m is an integer of from 0 to 2 inclusive;
n is an integer of from 2 to 5 inclusive;
Z is oxygen, sulfur or methylene; and
A is

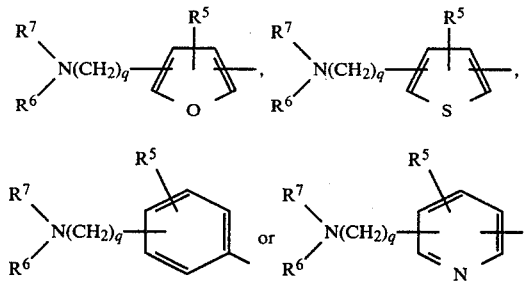

in which $R^5$ is hydrogen, (lower)alkyl or (lower)alkoxy, q is an integer of from 1 to 4 inclusive and $R^6$ and $R^7$ each are independently (lower)alkyl, (lower)alkoxy(lower)alkyl in which the (lower)alkoxy moiety is at least two carbon atoms removed from the nitrogen atom, or phenyl(lower)alkyl, and, when $R^6$ is hydrogen, $R^7$ also may be cyclo(lower)alkyl, or $R^6$ and $R^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; and nontoxic, pharmaceutically acceptable salts, hydrates and solvates thereof.

This invention also relates to processes for the preparation of the compounds of Formula I and to the intermediate compounds of Formula II.

The present invention includes within its scope all possible tautomeric forms, diastereoisomeric forms and optically active isomers of the compounds of Formula I as well as mixtures thereof. As used herein and in the claims, the term "(lower)alkyl" means a straight or branched chain alkyl group containing from 1 to 6 carbon atoms. The term "(lower)alkoxy" means a straight or branched chain alkoxy group containing from 1 to 4 carbon atoms. "Cyclo(lower)alkoxy" means a cycloalkyl group containing from 3 to 6 carbon atoms. The term "nontoxic pharmaceutically acceptable salts" means acid addition salts formed with acids such as hydrochloric, hydrobromic, nitric, sulfuric, acetic, propionic, fumaric, methanesulfonic, maleic, tartaric, citric, levulinic, benzoic, succinic and the like.

In the compounds of Formula I, $R^1$ preferably is hydrogen or (lower)alkyl, more preferably is hydrogen or methyl and most preferably is hydrogen. Substituent A preferably is the substituted phenyl moiety, substituted furyl moiety or substituted thienyl moiety shown above, and most preferably is the substituted phenyl moiety. Substituent Z preferably is sulfur or oxygen and, when A is the substituted phenyl moiety, Z preferably is oxygen. It is preferred that m is zero or 1 and n is 2 or 3, and that, when A is the substituted phenyl moiety, m is zero and n is 3. $R^5$ preferably is hydrogen or methyl and most preferably is hydrogen. It is preferred that q is 1. $R^6$ and $R^7$ preferably are (lower)alkyl or, taken together with the nitrogen atom to which they are attached, are pyrrolidino or piperidino.

The compounds of Formula I may be prepared by reaction of a compound of Formula II with sulfur monochloride ($S_2Cl_2$), sulfur dichloride ($SCl_2$) or chemical equivalents thereof, as follows:

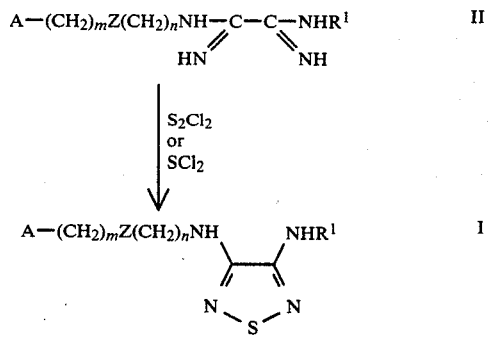

wherein A, m, Z, n and $R^1$ are as defined above. At least about 1 mole of $S_2Cl_2$ or $SCl_2$ should be used per mole of Compound II; it is preferred to use an excess of $S_2Cl_2$ or $SCl_2$, e.g. from about 2 to about 3 moles of $S_2Cl_2$ or $SCl_2$ per mole of Compound II. It has been found that $SCl_2$ often gives a cruder product and lower yield of purified product, and we usually prefer to use $S_2Cl_2$ for the reaction. The reaction temperature is not critical; we prefer to conduct the reaction at a temperature of from about 0° C. to about 50° C., and it is most convenient to conduct the reaction at ambient temperature. The reaction time is not critical and is dependent on temperature. We normally utilize a reaction time of from about 30 minutes to about 6 hours. At ambient temperature, reaction times of from about 1½ to 4 hours usually are preferred. The reaction may be conducted in an inert organic solvent, preferably a mixture of an inert organic solvent and dimethylformamide. Most preferably the reaction is conducted in dimethylformamide.

In a preferred embodiment of the invention, the compounds of Formula I have the structure

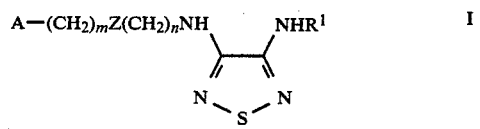

wherein $R^1$ is hydrogen or (lower)alkyl, m is 0 or 1, n is 2 or 3, Z is oxygen or sulfur and A is

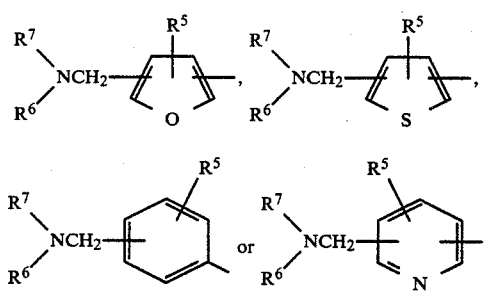

in which $R^5$ is hydrogen or methyl, and $R^6$ and $R^7$ each are independently methyl or ethyl, or when taken together with the nitrogen to which they are attached, $R^6$ and $R^7$ represent a pyrrolidino or piperidino ring; or a nontoxic pharmaceutically acceptable salt, hydrate or solvate thereof.

In a more preferred embodiment, the compounds of Formula I have the structure

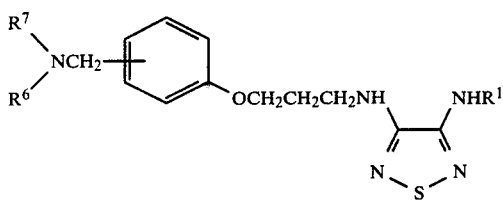
Ia wherein $R^1$ is hydrogen or methyl, and $R^6$ and $R^7$ each are methyl or, when taken together with the nitrogen atom to which they are attached, $R^6$ and $R^7$ represent a pyrrolidino or piperidino ring; or a nontoxic pharmaceutically acceptable salt, hydrate or solvate thereof.

In another more preferred embodiment, the compounds of Formula I have the structure

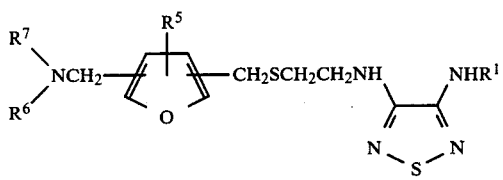
Ib wherein $R^1$ and $R^5$ each are independently hydrogen or methyl, and $R^6$ and $R^7$ each are independently methyl or ethyl; or a nontoxic pharmaceutically acceptable salt, hydrate or solvate thereof.

In another more preferred embodiment, the compounds of Formula I have the structure

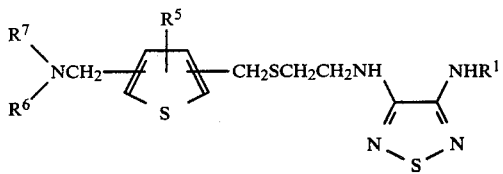
Ic wherein $R^1$ and $R^5$ each are independently hydrogen or methyl, and $R^6$ and $R^7$ each are independently methyl or ethyl; or a nontoxic pharmaceutically acceptable salt, hydrate or solvate thereof.

In another more preferred embodiment, the compounds of Formula I have the structure

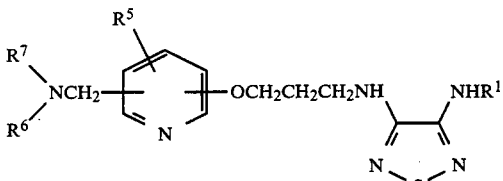
Id wherein $R^1$ and $R^5$ each are independently hydrogen or methyl, and $R^6$ and $R^7$ each are independently methyl or ethyl, or, when taken together with the nitrogen to which they, are attached, $R^6$ and $R^7$ represent piperidino; or a nontoxic pharmaceutically acceptable salt, hydrate or solvate thereof.

As presently envisaged, the most preferred compounds of Formula I are
(1) 3-amino-4-[3-(3-piperidinomethylphenoxy)-propylamino]-1,2,5-thiadiazole,
(2) 3-amino-4-{2-[(5-dimethylaminomethyl-2-furyl)methylthio]ethylamino}-1,2,5-thiadiazole;
(3) 3-amino-4-{2-[(5-dimethylaminomethyl-4-methyl-2-thienyl)methylthio]ethylamino}-1,2,5-thiadiazole,
(4) 3-amino-4-[3-(3-pyrrolidinomethylphenoxy)-propylamino]-1,2,5-thiadiazole,
(5) 3-methylamino-4-[3-(3-piperidinomethylphenoxy)-propylamino]-1,2,5-thiadiazole,
(6) 3-benzylamino-4-[3-(3-piperidinomethylphenoxy)-propylamino]-1,2,5-thiadiazole,
(7) 3-amino-4-{2-[(5-dimethylaminomethyl-3-thienyl)-methylthio]ethylamino}-1,2,5-thiadiazole,
(8) 3-amino-4-{2-[(5-piperidinomethyl-3-thienyl)methylthio]ethylamino}-1,2,5-thiadiazole,
(9) 3-amino-4-[3-(6-piperidinomethyl-2-pyridyloxy)-propylamino]-1,2,5-thiadiazole and
(10) 3-amino-4-[3-(4-piperidinomethyl-2-pyridyloxy)-propylamino]-1',2,5-thiadiazole; and their nontoxic, pharmaceutically acceptable salts, hydrates and solvates.

The intermediates of Formula II used in the preparation of the compounds of Formula I may themselves be prepared by various procedures. In one procedure, the corresponding 3-(amino or substituted amino)-4-(substituted amino)-1,2,5-thiadiazole 1-oxide of Formula III is treated with a strong mineral acid (preferably HCl) to produce the compound of Formula II.

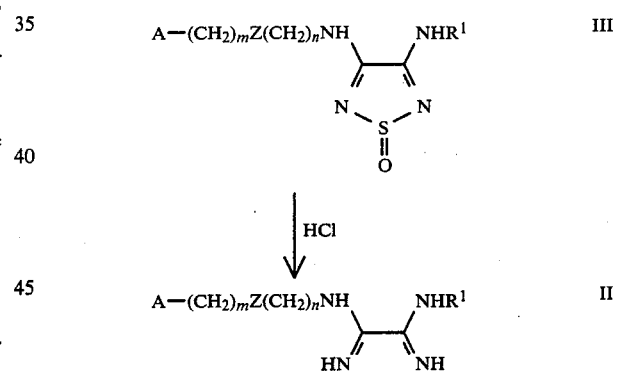

The reaction may be conducted in an inert solvent and preferably is conducted in methanol. Reaction temperature is not critical; it most conveniently is conducted at room temperature. The compounds of Formula III are known or may readily be prepared by the procedures described in our published United Kingdom Patent Application No. 2,067,987.

In an alternate procedure, the compounds of Formula II may be prepared by the following reaction scheme. The

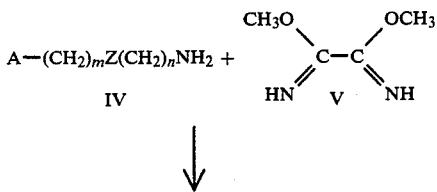

-continued

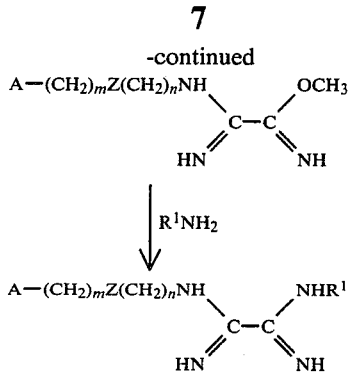

reaction may be conducted in an inert solvent and preferably is conducted in methanol. The starting materials of Formula IV are known or may be readily prepared by known procedures, e.g. as by procedures described in our published United Kingdom Patent Application No. 2,067,987.

In another aspect, this invention relates to novel intermediates of the formula

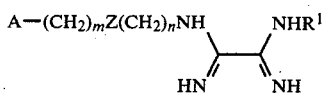

wherein $R^1$ is hydrogen, (lower)alkyl, 2-fluoroethyl, 2,2,2-trifluoroethyl, allyl, propargyl,

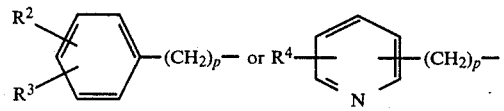

in which p is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;
m is an integer of from 0 to 2 inclusive;
n is an integer of from 2 to 5 inclusive;
Z is oxygen, sulfur or methylene; and
A is

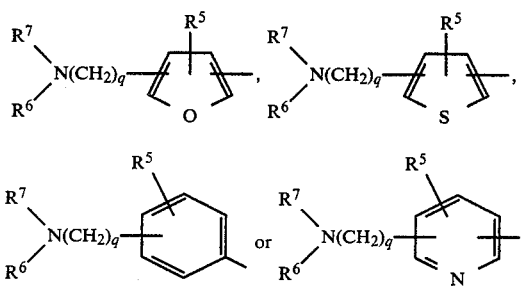

in which $R^5$ is hydrogen, (lower)alkyl or (lower)alkoxy, q is an integer of from 1 to 4 inclusive and $R^6$ and $R^7$ each are independently (lower)alkyl, (lower)alkoxy(-lower)alkyl in which the (lower)alkoxy moiety is at least two carbon atoms removed from the nitrogen atom, or phenyl(lower)alkyl, and, when $R^6$ is hydrogen, $R^7$ also may be cyclo(lower)alkyl, or $R^6$ and $R^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; or a salt, hydrate or solvate thereof.

In a preferred embodiment, the intermediates of Formula II have the structure

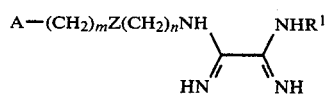

wherein $R^1$ is hydrogen or (lower)alkyl, m is 0 or 1, n is 2 or 3, Z is oxygen or sulfur and A is

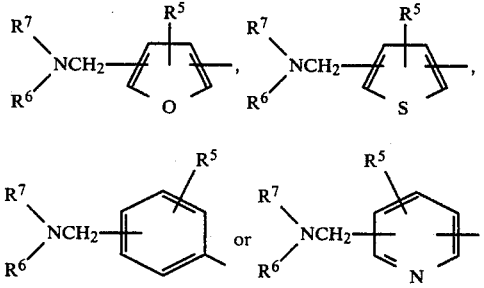

in which $R^5$ is hydrogen or methyl, and $R^6$ and $R^7$ each are independently methyl or ethyl, or when taken together with the nitrogen to which they are attached, $R^6$ and $R^7$ represent a pyrrolidino or piperidino ring; or a nontoxic pharmaceutically acceptable salt, hydrate or solvate thereof.

In another preferred embodiment, the intermediates of Formula II have the structure

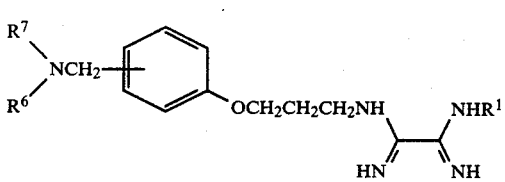

wherein $R^1$ is hydrogen or methyl, and $R^6$ and $R^7$ each are methyl or, when taken together with the nitrogen atom to which they are attached, $R^6$ and $R^7$ represent a pyrrolidino or piperidino ring; or a salt, hydrate or solvate thereof.

In another preferred embodiment, the intermediates of Formula II have the structure

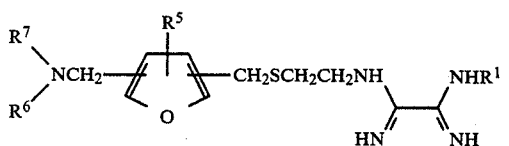

wherein $R^1$ and $R^5$ each are independently hydrogen or methyl; and $R^6$ and $R^7$ each are independently methyl or ethyl; or a salt, hydrate or solvate thereof.

In another preferred embodiment, the intermediates of Formula II have the structure

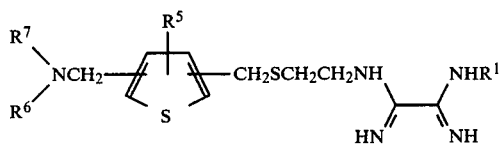

IIc wherein $R^1$ and $R^5$ each are independently hydrogen or methyl, and $R^6$ and $R^7$ each are independently methyl or ethyl; or a salt, hydrate or solvate thereof.

In another preferred embodiment, the intermediates of Formula II have the structure

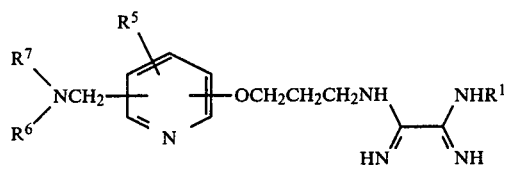

IId wherein $R^1$ and $R^5$ each are independently hydrogen or methyl, and $R^6$ and $R^7$ each are independently methyl or ethyl, or, when taken together with the nitrogen to which they are attached, $R^6$ and $R^7$ represent piperidino; or a salt, hydrate or solvate thereof.

As presently envisaged, the most preferred intermediates of Formula II are (1) N-[3-(3-piperidinomethylphenoxy)propyl]ethanediimidamide,
(2) N-{2-[(5-dimethylaminomethyl-2-furyl)methylthio]ethyl}ethanediimidamide,
(3) N-{2-[(5-dimethylaminomethyl-4-methyl-2-thienyl)methylthio]ethyl≡ethanediimidamide,
(4) N-[3-(3-pyrrolidinomethylphenoxy)propyl]ethanediimidamide,
(5) N-{2-[(5-dimethylaminomethyl-3-thienyl)methylthio]ethyl}ethanediimidamide,
(6) N-{2-[(5-piperidinomethyl-3-thienyl)methylthio]ethyl}ethanediimidamide,
(7) N-[3-(6-piperidinomethyl-2-pyridyloxy)propyl]ethanediimidamide and
(8) N-[3-(4-piperidinomethyl-2-pyridyloxy)propyl]ethanediimidamide;

or a salt, hydrate or solvate thereof.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed (and the number of times to be administered per day) is within the discretion of the physician, and may be varied by titration of the dosage to the particular circumstances of the specific patient. With the preferred compounds of this invention, each oral dosage unit will contain the active ingredient in an amount of from about 2 mg to about 300 mg, and most preferably from about 4 mg to about 100 mg. The active ingredient will preferably be administered in equal doses from one to four times a day.

Histamine $H_2$-receptor antagonists have been shown to be effective inhibitors of gastric secretion in aimals and man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1, 8001 (1977). Some of the preferred compounds of this invention have been compared with cimetidine in various tests and have been found to be more potent than cimetidine both as an histamine $H_2$-receptor antagonist in isolated guinea pig right atria and as an inhibitor of gastric acid secretion in rats and dogs.

DETERMINATION OF GASTRIC ANTISECRETORY ACTIVITY IN THE GASTRIC FISTULA RAT

Male Long Evans rats weighing about 240-260 grams at the time of cannula implantation are used. The design and implantation of the stainless steel cannula into the anterior wall of the fore-stomach are carried out essentially as described by Pare et al. [Laboratory Animal Science, 27, 244 (1977)]. The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30-40 mL of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way the rat is not restricted and can move freely about the cage during collection periods. The remainder of the assay is carried out as described by Ridley et al. [Research Comm. Chem. Path. Pharm., 17, 365 (1977)].

Gastric secretions collected during the first hour after washing the stomach are discarded as they may be contaminated. For oral evaluation, the catheter is then removed from the cannula and replaced with the plugging screw. Water (2 mL/kg) is administered orally via gastric intubation and the animal is returned to the cage for 45 minutes. After this time the plugging screw is removed and replaced with a catheter to which a small plastic vial has been attached to collect the gastric secretions. A two-hour sample is collected (this represents the control secretion), the catheter is removed and replaced with the plugging screw. The test drug is now administered orally in a volume of 2 mL/kg via gastric intubation. Forty-five minutes later the plugging screw is again removed, replaced with the catheter attached to a small plastic vial and another 2-hour sample is collected. The secretions in the second sample are compared to those of the control sample in order to determine the effects of the test drug.

When test compounds are to be evaluated parenterally, the animal is injected ip or sc with the test compound vehicle in a volume of 2 mL/kg immediately after discarding the initial 60-minute collection. A two-hour sample is collected (control secretion) and the animals are injected either ip or sc with the test compound in a volume of 2 mL/kg. An additional two-hour sample is collected and its secretions are compared to those of the control period to determine drug effects.

The samples are centrifuged and placed in a graduated centrifuge tube for volume determination. Titratable acidity is measured by titrating a one-mL sample to pH 7.0 with 0.02N NaOH, using an Autoburet and an electrometric pH meter (Radiometer). Titratable acid output is calculated in micro-equivalents by multiplying the volume in milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for determination of a dose response curve.

TABLE 1

| Gastric Antisecretory Activity in the Gastric Fistula Rat | | |
|---|---|---|
| Compound | $ED_{50}$ sc μmoles/kg | Potency Ratio (cimetidine = 1.0) |
| cimetidine | 3.48 (1.68–5.75)* | 1.0 |
| Example 1 | 0.094 (0.043–0.20) | 37 |
| Example 2 | 0.77 (0.45–1.4) | 4.5 |
| Example 3 | ~0.5 | ~7 |
| Example 4 | 0.18 (0.10–0.36) | 20 |

*95% confidence limits

HISTAMINE H₂-RECEPTOR ANTAGONISM-ISOLATED GUINEA PIG ATRIA ASSAY

Histamine produces concentration-related increases in the contractile rate of isolated, spontaneously beating guinea pig right atria. Black et al., Nature, 236, 385 (1972), described the receptors involved in this effect of histamine as histamine H₂-receptors when they reported the properties of burimamide, a competitive antagonist of these receptors. Subsequent investigations by Hughes and Coret, Proc. Soc. Exp. Biol. Med., 148, 127 (1975) and Verma and McNeill, J. Pharmacol. Exp. Ther., 200, 352 (1977) support the conclusion of Black and coworkers that the positive chronotropic effect of histamine in isolated guinea pig right atria is mediated via histamine H₂-receptors. Black et al., Agents and Actions, 3, 133 (1973) and Brimblecombe et al., Fed. Proc., 35, 1931 (1976) have utilized isolated guinea pig right atria as a means for comparing the activities of histamine H₂-receptor antagonists. The present comparative studies were carried out using a modification of the procedure reported by Reinhardt et al., Agents and Actions, 4, 217 (1974).

Male Hartley strain guinea pigs (350–450 gm) were sacrificed by a blow on the head. The heart was excised and placed in a Petri dish of oxygenated (95%, $O_2$, 5% $CO_2$) modified Krebs solution (g/liter: NaCl 6.6, KCl 0.35, $MgSO_4.7H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-0) attached to each end. The atrium was suspended in a 20 ml muscle chamber containing oxygenated modified Krebs solution maintained at 32° C. Atrial contractions were recorded isometrically by means of a Grass FT 0.03 force displacement transducer and recordings of contractile force and rate were made with a Beckman RP Dynograph.

A resting tension of 1 g was applied to the atrium and it was allowed to equilibrate for 1 hour. At the end of the equilibration period a submaximal concentration of histamine dihydrochloride ($3 \times 10^{-6}$M) was added to the bath and washed out to prime the tissue. Histamine was then added to the bath in a cumulative fashion using ½ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$M concentration. The histamine was washed out several times and the atrium allowed to return to control rate. The test compound was then added at appropriate molar concentrations and, after a 30-minute incubation, the histamine dose response was repeated adding higher concentrations as needed.

The dissociation constants ($K_B$) were derived from Schild plots by the method of Arunlakshana, O. and Schild, H. O. [Br. J. Pharmacol. 14, 48 (1959)] using at least three dose levels. Parallel shifts in dose-response curves were obtained without depressing the maximal response at the antagonist concentrations utilized, and the results are shown in Table 2.

TABLE 2

| Activity in Isolated Guinea Pig Right Atria | | | |
|---|---|---|---|
| Compound | N | $K_B$ (μmoles) | Potency Ratio (cimetidine = 1.0) |
| cimetidine | 20 | 0.41 (.21–.64)* | 1.0 |
| Example 1 | 12 | 0.003 (.001–.004) | 137 |
| Example 4 | 11 | 0.004 (.001–.010) | 102 |

*95% confidence limits

As described in U.S. patent application Ser. No. 475,985 (SY-1751), filed Mar. 16, 1983 now U.S. Pat. No. 4,440,933, (concurrently) by our colleague Thomas A. Montzka, the compounds of Formula I also may be prepared by ring closure of a compound of Formula II with N,N'-thiobisphthalimide having the formula

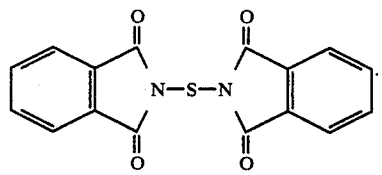

The use of N,N'-thiobisphthalimide instead of $S_2Cl_2$ or $SCl_2$ for the ring closure reaction results in both purer and higher crude yields of the compounds of Formula I.

The crude products of Formula I thereby produced normally are pure enough to form crystalline salts directly without prior chromatographic purification.

In this process, the starting diimidamide of Formula II is reacted with about an equimolar amount of N,N'-thiobisphthalimide in an inert organic solvent such as $CH_2Cl_2$. Preferably the starting diimidamide is used in the form of its trihydrochloride salt, in which case three molar equivalents of an amine, such as triethylamine, are added to the reaction mixture to neutralize the trihydrochloride salt. The reaction may be conducted by stirring at room temperature for about an hour to insure completeness of the reaction. The phthalimide which precipitates from the reaction mixture is then extracted with a strong base (e.g. 10–20% aqueous KOH), and the organic solvent layer is dried, filtered and concentrated to yield the crude compound of Formula I. The N,N'-thiobisphthalimide used in the reaction is a known compound which may be prepared as described in the Canadian Journal of Chemistry, 44, 2111–2113 (1966), or as described below in Preparation No. 1.

PREPARATION NO. 1

N,N'-Thiobisphthalimide

A cooled (0° C.) solution of phthalimide (14.7 g, 0.1 mole) in 80 ml of dimethylformamide (DMF) was treated dropwise with sulfur dichloride (5.15 g, 0.05 mole). After the addition, the mixture was allowed to warm to 20° C. with stirring over four hours. The solid was collected and dried to give 12.5 g of the title compound as a DMF solvate, mp 301°–315° C. Both ir and nmr spectra are consistant for structure.

Anal. Calc'd. for $C_{16}H_8N_2O_4S \cdot C_3H_7NO$: C, 57.42; H, 3.80; N, 10.57; S, 8.07. Found: C, 57.50; H, 3.80; N, 10.29; S, 8.57.

The DMF solvate can be removed by recrystallization of the above material from chloroform; mp of the DMF-free product was 320°–325° C. The nmr spectrum shows that the DMF has been removed.

Anal. Calc'd. for $C_{16}H_8N_2O_4S$: C, 59.25; H, 2.49; N, 8.64; S, 9.89. Found: C, 59.21; H, 2.21; N, 8.91; S, 10.14.

EXAMPLE 1

3-Amino-4-[3-(3-piperidinomethylphenoxy)-propylamino]-1,2,5-thiadiazole

A.

N-[3-(3-Piperidinomethylphenoxy)propyl]ethanediimidamide trihydrochloride

A suspension of 3-amino-4-[3-(3-piperidinomethylphenoxy)propylamino]-1,2,5-thiadiazole 1-oxide (17.1 g; 47.0 mmoles) [prepared according to published United Kingdom Patent Application No. 2,067,987] in 450 mL of methanol was treated with 38 mL of concentrated HCl. The resultant solution was stirred for 3 hours at ambient temperature. Concentration of the solution followed by azeotropic removal of water with absolute ethanol gave colorless crystals. These were suspended in 200 mL of absolute ethanol, filtered and dried under vacuum to give 16.6 g (82.6%) of the title compound, m.p. 205°–222° C. (dec.). Recrystallization from 50% methanol-ethyl acetate gave an analytical sample, m.p. 206°–216° C. (dec.).

Anal. Calc'd for $C_{17}H_{27}N_5O \cdot 3HCl$: C, 47.84; H, 7.08; N, 16.41. Found: C, 47.56; H, 7.18; N, 16.75.

B.

3-Amino-4-[3-(3-piperidinomethylphenoxy)-propylamino]-1,2,5-thiadiazole

A stirred suspension of N-[3-(3-piperidinomethylphenoxy)propyl]ethanediimidamide trihydrochloride (2.13 g, 5.0 mmoles) [prepared in Step A] in 20 mL of dimethylformamide (DMF) was treated with sulfur monochloride (2.02 g, 15.0 mmoles) and stirred for 4 hours. The resultant mixture was poured cautiously into 200 mL of water and made basic with $K_2CO_3$. This was extracted with 3×50 mL portions of methylene chloride and, after drying over $MgSO_4$ and concentration, 2.1 g of a dark gum containing the product was obtained. The product was purified by preparative high pressure liquid chromatography on silica using $CH_2Cl_2(100):2$-propanol(10):$NH_4OH(0.5)$ as the mobile phase. The appropriate fractions yielded 0.89 g of the title compound which gave, with fumaric acid in n-propanol, 0.76 g (21.4%) of the title compound as a crystalline fumarate salt, m.p. 187°–187.5° C. HPLC indicated a purity of >99%.

Anal. Calc'd for $(C_{17}H_{25}N_5OS)_2 \cdot C_4H_4O_4$: C, 56.27; H, 6.71; N, 17.27; S, 7.90. Found: C, 56.09; H, 6.36; N, 16.98; S, 8.08.

A portion of the fumarate was suspended in water, neutralized with $K_2CO_3$ and extracted with $CH_2Cl_2$. The $CH_2Cl_2$ was concentrated and the free base of the title compound crystallized out; m.p. 43°–47° C. A portion of the free base was converted to the hydrochloride salt, m.p. 138°–140° C.

Anal. Calc'd for $C_{17}H_{25}N_5OS \cdot HCl$: C, 53.18; H, 6.83; N, 18.24; S, 8.35. Found: C, 53.14; H, 6.88; N, 18.49; S, 8.74.

EXAMPLE 2

3-Amino-4-{2-[(5-dimethylaminomethyl-2-furyl)methylthio]ethylamino}-1,2,5-thiadiazole

A.

N-{2-[(5-Dimethylaminomethyl-2-furyl)methylthio]ethyl}ethanediimidamide trihydrochloride hydrate A suspension of 3-amino-4-{2-[(5-dimethylaminomethyl-2-furyl)methylthio]ethylamino}-1,2,5-thiadiazole 1-oxide (6.59 g; 20.0 mmoles) [prepared according to published United Kingdom Patent Application No. 2,067,987] in 200 mL of methanol was warmed slightly to achieve complete solution, then treated with 13.3 mL of concentrated HCl. After stirring at ambient temperature for 2.5 hours, the solution was concentrated and the residue was triturated with 70 mL of absolute ethanol. The crystals were collected by filtration and dried under vacuum to give 4.3 g (52%) of the title compound, m.p. 166°–169° C. (dec.).

Anal. Calc'd for $C_{12}H_{21}N_5OS \cdot 3HCl \cdot H_2O$: C, 35.08; H, 6.38; N, 17.05; S, 7.80. Found: C, 34.85; H, 6.24; N, 17.45; S, 7.97.

B.

3-Amino-4-{2-[(5-dimethylaminomethyl-2-furyl)methylthio]ethylamino}-1,2,5-thiadiazole To a stirred suspension of N-{2-[(5-dimethylaminomethyl-2-furyl)methylthio]ethyl}ethanediimidamide trihydrochloride hydrate (12.3 g; 30.0 mmoles) [prepared in Step A] in 150 mL of DMF was added 7.2 mL of sulfur monochloride (12.1 g; 90 mmoles). After stirring for 4 hours at ambient temperature, approximately half of the DMF was removed at reduced pressure. The remaining black solution was poured into 1 liter of water, made basic with K$_2$CO$_3$ and extracted first with ethyl acetate and then with chloroform. After drying over MgSO$_4$, filtration and concentration, 9.0 g of a black gum containing the product was obtained. This was purified by preparative high pressure liquid chromatography on silica using ethyl acetate(100):2-propanol(10):NH$_4$OH(0.5) as the mobile phase. The appropriate fractions yielded 1.24 g of the title compound as a gum.

Treatment of part of this product with an equivalent amount of 2N HCl in methanol yielded the hydrochloride salt of the title compound.

Anal. Calc'd for C$_{12}$H$_{19}$N$_5$S$_2$O·HCl: C, 41.18; H, 5.76; N, 20.02; S, 18.33. Found (corr. for 1.65% H$_2$O): C, 40.54; H, 5.70; N, 19.39; S, 18.44.

Treatment of the product with an equivalent amount of cyclohexylsulfamic acid in acetone yielded the cyclohexyl-sulfamate salt of the title compound, m.p. 93°–95° C.

Anal. Calc'd for C$_{12}$H$_{19}$N$_5$S$_2$O·C$_6$H$_{13}$NO$_3$S: C, 43.88; H, 6.55; N, 17.06; S, 19.53. Found: C, 43.77; H, 6.17; N, 17.21; S, 19.58.

EXAMPLE 3

3-Amino-4-{2-[(5-dimethylaminomethyl-4-methyl-2-thienyl)methylthio]ethylamino}-1,2,5-thiadiazole

A.

N-{2-[(5-Dimethylaminomethyl-4-methyl-2-thienyl)-methylthio]ethyl}ethanediimidamide trihydrochloride A stirred solution of 3-amino-4-{2-[(5-dimethylaminomethyl-4-methyl-2-thienyl)methylthio]ethylamino}-1,2,5-thiadiazole 1-oxide (17.9 g, 50.0 mmoles) [prepared according to the general procedure described in published United Kingdom Patent Application No. 2,067,987] in 500 mL of methanol was treated with 33.3 mL of concentrated HCl. After stirring for 3 hours, the reaction mixture was concentrated and excess water was removed by azeotropic concentration with absolute ethanol to give an almost colorless crystalline residue. The residue was triturated with 200 mL of absolute ethanol at 0° C., filtered and dried to give 16.9 g (80%) of the title compound, m.p. 206°–220° C. (dec.). Recrystallization from 50% methanol-ethyl acetate gave a product having m.p. 210°–221° C. (dec.).

Anal. Calc'd for C$_{13}$H$_{23}$N$_5$S$_2$·3HCl: C, 36.92; H, 6.20; N, 16.56; S, 15.17. Found: C, 36.76; H, 6.33; N, 16.97; S, 15.54.

B.

3-Amino-4-{2-[(5-dimethylaminomethyl-4-methyl-2-thienyl)methylthio]ethylamino}-1,2,5-thiadiazole To a stirred suspension of N-{2-[(5-dimethylaminomethyl-4-methyl-2-thienyl)methylthio]ethyl}ethanediimidamide trihydrochloride (6.34 g; 15.0 mmoles) [prepared in Step A] in 60 mL of DMF was added 6.1 g (45.0 mmoles) of sulfur monochloride. After stirring for 4 hours at ambient temperature, the reaction mixture was poured into 800 mL of water, made basic with K$_2$CO$_3$, and extracted several times with 100 mL-portions of methylene chloride. The extracts were dried over MgSO$_4$, filtered, and concentrated to give 3.4 g of a black gum containing the product. The product was purified by preparative high pressure liquid chromatography on silica using CH$_2$Cl$_2$(100):2-propanol(10):NH$_4$OH(0.5) as the mobile phase. Further purification was achieved by an additional preparative high pressure liquid chromatography on silica using CH$_2$Cl$_2$(100):CH$_3$OH(2.5):NH$_4$OH(0.5) as the mobile phase. The appropriate fractions yielded the title compound (purity ~98%). Treatment of the product with an equivalent amount of 2N HCl gave the hydrochloride salt of the title compound.

Anal. Calc'd for C$_{13}$H$_{21}$N$_5$S$_3$·HCl: C, 41.09; H, 5.84; N, 18.43; S, 25.32. Found (corr. for 0.51% H$_2$O): C, 40.78; H, 5.63; N, 18.31; S, 25.44.

EXAMPLE 4

3-Amino-4-[3-(3-pyrrolidinomethylphenoxy)-propylamino]-1,2,5-thiadiazole

A.

N-[3-(3-Pyrrolidinomethylphenoxy)propyl]-ethanediimidamide trihydrochloride

A suspension of 3-amino-4-[3-(3-pyrrolidinomethylphenoxy)propylamino]-1,2,5-thiadiazole 1-oxide (13.4 g; 38.3 mmoles) [prepared according to published United Kingdom Patent Application No. 2,067,987] in 350 mL of methanol was treated with 25.5 mL of concentrated HCl. The resultant solution was stirred for 3 hours at ambient temperature. Concentration of the solution followed by azeotropic removal of water with absolute ethanol gave the product. The crystalline residue was triturated with 150 mL of absolute ethanol, filtered and dried to give 10.8 g of the title compound, m.p. 195°–203° C. (dec.).

Anal. Calc'd for C$_{16}$H$_{25}$N$_5$O·3HCl: C, 46.55; H, 6.84; N, 16.97. Found: C, 46.55; H, 6.93; N, 16.93.

B.

3-Amino-4-[3-(3-pyrrolidinomethylphenoxy)-propylamino]-1,2,5-thiadiazole

A stirred suspension of N-[3-(3-pyrrolidinomethylphenoxy)propyl]ethanediimidamide trihydrochloride (8.25 g; 20.0 mmoles) [prepared in Step A] in 80 mL of DMF was treated with sulfur monochloride (5.4 g; 40.0 mmoles) and stirred under a nitrogen atmosphere for 3 hours. Concentration of the reaction mixture gave a dark gum which was suspended in 500 mL of water, made basic with K$_2$CO$_3$ and extracted with 3×100 mL of methylene chloride. The extracts were dried over MgSO$_4$, filtered and concentrated to give 7.5 g of a dark gum containing the product. The product was purified by preparative high pressure liquid chromatography on silica using CH$_2$Cl$_2$(100):2-propanol(5):NH$_4$OH(0.5) as the mobile phase. Fractions containing the desired product were combined and concentrated to give 1.64 g (24.6%) of the purified title product. Treatment of the product in absolute ethanol with an equivalent amount of 2N HCl gave the hydrochloride salt of the title compound (1.13 g); m.p. 138°–140° C.

Anal. Calc'd for C$_{16}$H$_{23}$N$_5$OS·HCl: C, 51.95; H, 6.54; N, 18.93; S, 8.67. Found: C, 51.97; H, 6.36; N, 18.63; S, 8.76.

EXAMPLE 5

The general procedure of Example 1, Steps A and B, is repeated except that the 3-amino-4-[3-(3-piperidinomethylphenoxy)propylamino]-1,2,5-thiadiazole 1-oxide utilized therein is replaced by an equimolar amount of (a) 3-amino-4-[3-(3-dimethylaminomethylphenoxy)-propylamino]-1,2,5-thiadiazole 1-oxide, (b) 3-amino-4-[3-(3-diethylaminomethylphenoxy)-propylamino]-1,2,5-thiadiazole 1-oxide, (c)  3-amino-4-[3-(3-(2-methylpyrrolidino)methylphenoxy]propylamino}-1,2,5-thiadiazole 1-oxide,
(d)  3-amino-4-{3-[3-(3-methylpyrrolidino)methylphenoxy]propylamino}-1,2,5-thiadiazole 1-oxide,
(e)  3-amino-4-{3-[3-(4-methylpiperidino)methylphenoxy]propylamino}-1,2,5-thiadiazole 1-oxide,
(f)  3-amino-4-[3-(3-morpholinomethylphenoxy)propylamino]-1,2,5-thiadiazole 1-oxide,
(g)  3-amino-4-{3-[3-(N-methylpiperazino)methylphenoxy]propylamino}-1,2,5-thiadiazole 1-oxide,
(h)  3-amino-4-[3-(3-diallylaminomethylphenoxy)propylamino]-1,2,5-thiadiazole 1-oxide,
(i)  3-amino-4-[3-(3-hexamethyleneiminomethylphenoxy)propylamino]-1,2,5-thiadiazole 1-oxide,
(j)  3-amino-4-[3-(3-heptamethyleneiminomethylphenoxy)propylamino]-1,2,5-thiadiazole 1-oxide,
(k)  3-amino-4-{3-[3-(3-azabicyclo[3.2.2]non-3-yl)methylphenoxy]propylamino}-1,2,5-thiadiazole 1-oxide and
(l)  3-amino-4-{3-[3-(3-pyrrolino)methylphenoxy]propylamino}-1,2,5-thiadiazole 1-oxide, respectively, and there is thereby produced
(a)  3-amino-4-[3-(3-dimethylaminomethylphenoxy)propylamino]-1,2,5-thiadiazole,
(b)  3-amino-4-[3-(3-dimethylaminomethylphenoxy)propylamino]-1,2,5-thiadiazole,
(c)  3-amino-4-{3-[3-(2-methylpyrrolidino)methylphenoxy]propylamino}-1,2,5-thiadiazole,
(d)  3-amino-4-{3-[3-(3-methylpyrrolidino)methylphenoxy]propylamino}-1,2,5-thiadiazole,
(e)  3-amino-4-{3-[3-(4-methylpiperidino)methylphenoxy]propylamino}-1,2,5-thiadiazole,
(f)  3-amino-4-[3-(3-morpholinomethylphenoxy)propylamino]-1,2,5-thiadiazole,
(g)  3-amino-4-{3-[3-(N-methylpiperazino)methylphenoxy]propylamino}-1,2,5-thiadiazole,
(h)  3-amino-4-[3-(3-diallylaminomethylphenoxy)propylamino]-1,2,5-thiadiazole,
(i)  3-amino-4-[3-(3-hexamethyleneiminomethylphenoxy)propylamino]-1,2,5-thiadiazole,
(j)  3-amino-4-[3-(3-heptamethyleneiminomethylphenoxy)propylamino]-1,2,5-thiadiazole,
(k)  3-amino-4-{3-[3-(3-azabicyclo[3.2.2]non-3-yl)methylphenoxy]propylamino}-1,2,5-thiadiazole and
(l)  3-amino-4-{3-[3-(3-pyrrolino)methylphenoxy]propylamino}-1,2,5-thiadiazole, respectively.

EXAMPLE 6

3-Amino-4-[3-(3-piperidinomethylphenoxy)propylamino]-1,2,5-thiadiazole

This is a variation of Example 1, Step B, utilizing less sulfur monochloride and a shorter reaction time.

To a stirred suspension of N-[3-(3-piperidinomethylphenoxy)propyl]ethanediimidamide trihydrochloride (12.08 g; 28.3 mmoles) in 120 mL of DMF was added sulfur monochloride (7.64 g; 56.6 mmoles) and the mixture was stirred under an $N_2$ atmosphere for 3 hours. The DMF was removed at reduced pressure to leave a black gum which was suspended in water, made basic with $K_2CO_3$ and extracted with 3×100 mL portions of $CH_2Cl_2$. The combined extracts were dried over $MgSO_4$, filtered and concentrated to a black gum. This gum was purified by preparative high pressure liquid chromatography on silica using $CH_2Cl_2(100):2$-propanol(5):$NH_4OH$(0.5) as the mobile phase. The appropriate fractions yielded 3.1 g of the title product as a dark oil which gave, with fumaric acid in n-propanol, 2.66 g (23.2%) of the title compound as a crystalline fumarate salt, m.p. 186°–186.5° C. HPLC indicated a purity of 99%.

Anal. Calc'd for $(C_{17}H_{25}N_5OS)_2 \cdot C_4H_4O_4$: C, 56.27; H, 6.71; N, 17.27; S, 7.90. Found: C, 56.27; H, 6.96; N, 17.31; S, 7.98.

EXAMPLE 7

3-Amino-4-[3-(3-piperidinomethylphenoxy)propylamino]-1,2,5-thiadiazole

This is a variation of Example 1, Step B, utilizing sulfur dichloride instead of sulfur monochloride.

To a stirred suspension of N-[3-(3-piperidinomethylphenoxy)propyl]ethanediimidamide trihydrochloride (854 mg; 2 mmoles) in 6 mL of DMF under $N_2$ in an ice bath was added $SCl_2$ (206 mg; 2 mmoles) in 2 mL of DMF. The reaction mixture was stirred at ambient temperature and the title compound was produced.

EXAMPLE 8

3-Methylamino-4-[3-(3-piperidinomethylphenoxy)propylamino]-1,2,5-thiadiazole

A.

N-Methyl-N'-[3-(3-piperidinomethylphenoxy)propyl]ethanediimidamide trihydrochloride A suspension of 3-methylamino-4-[3-(3-piperidinomethylphenoxy)propylamino]-1,2,5-thiadiazole 1-oxide (4.13 g; 10.9 mmoles) [prepared according to published United Kingdom Patent Application No. 2,067,987] in 95 ml of methanol was treated with 7.2 ml of concentrated HCl. After stirring at ambient temperature for 3 hours, the solution was concentrated and the residue was triturated with acetone, filtered and dried to give 4.35 g (90.4%) of product. A sample was recrystallized from aqueous isopropyl alcohol to give the title compound, mp 207°–225° C. (dec.).

Anal. Calc'd for $C_{18}H_{29}N_5O \cdot 3HCl$: C, 49.03; H, 7.33; N, 15.89. Found (corr. for 0.94% $H_2O$): C, 49.37; H, 7.35; N, 15.71.

B.

3-Methylamino-4-[3-(3-piperidinomethylphenoxy)propylamino]-1,2,5-thiadiazole

A mixture of N-methyl-N'-[3-(3-piperidinomethylphenoxy)propyl]ethanediimidamide trihydrochloride (3.74 g; 8.47 mmoles) [prepared in Step A], 34 ml of $CH_2Cl_2$ and 3.5 ml of triethylamine was treated with N,N'-thiobisphthalimide (DMF solvate) (3.36 g; 8.46 mmoles) and stirred for one hour. The mixture was washed with 30 ml of 10% KOH, dried ($MgSO_4$), filtered, diluted with toluene and concentrated to give 3.6 g of the product. The product was purified by flash chromatography on 90 g of silica gel (230–400 mesh) using ethyl acetate-methanol (95:5) as the eluent to give 1.9 g (62%) of the title compound. Treatment of the product with an equivalent amount of aqueous HCl in 1-propanol gave the hydrochloride salt of the title compound, mp 163.5°–164.5° C.

Anal. Calc'd for $C_{18}H_{27}N_5OS \cdot HCl$: C, 54.32; H, 7.04; N, 17.60; S, 8.06; Cl, 8.91. Found: C, 54.35; H, 7.07; N, 17.64; S, 8.36; Cl, 8.86.

EXAMPLE 9

3-Benzylamino-4-[3-(3-piperidinomethylphenoxy)-propylamino]-1,2,5-thiadiazole

A.

N-Benzyl-N'-[3-(3-piperidinomethylphenoxy)propyl]ethanediimidamide trihydrochloride A suspension of 3-benzylamino-4-[3-(3-piperidinomethylphenoxy)propylamino]-1,2,5-thiadiazole 1-oxide (5.14 g; 11.3 mmoles) [prepared according to published United Kingdom Patent Application No. 2,067,987] in 100 ml of methanol was treated with 7.55 ml of concentrated HCl. After stirring at ambient temperature for 3 hours, the solution was concentrated and the residue was triturated with acetone, filtered and dried to give 5.16 g (88%) of the title compound, mp 187°–205° C. (dec.).

Anal. Calc'd for $C_{24}H_{33}N_5O \cdot 3HCl$: C, 55.75; H, 7.03; N, 13.55; Cl, 20.57. Found: C, 54.88; H, 6.75; N, 13.33; Cl, 20.20.

B.

3-Benzylamino-4-[3-(3-piperidinomethylphenoxy)-propylamino]-1,2,5-thiadiazole

A mixture of N-benzyl-N'-[3-(3-piperidinomethylphenoxy)propyl]ethanediimidamide trihydrochloride (4.73 g; 9.16 mmoles) [prepared in Step A], 45 ml of $CH_2Cl_2$ and 3.8 ml of triethylamine was treated with N,N'-thiobisphthalimide (DMF solvate) (3.64 g; 9.16 mmoles) and stirred for one hour. The mixture was washed with 44 ml of 10% KOH, dried (MgSO$_4$), filtered, diluted with toluene and concentrated. The residue was chromatographed by flash chromatography on 110 g of silica gel (230–400 mesh) using ethyl acetate as the eluent to give 3.1 g (77%) of the title compound. Treatment of the product with an equivalent amount of aqueous HCl in 2-propanol gave the hydrochloride salt of the title compound, mp 138°–141° C.

Anal. Calc'd. for $C_{24}H_{31}N_5OS \cdot HCl$: C, 60.80; H, 6.80; N, 14.77; S, 6.76; Cl, 7.48. Found: C, 60.53; H, 6.64; N, 14.99; S, 6.91; Cl, 7.47.

EXAMPLE 10

3-Amino-4-[3-(3-piperidinomethylphenoxy)-propylamino]-1,2,5-thiadiazole

This is a variation of Example 1, Step B, utilizing N,N'-thiobisphthalimide instead of sulfur monochloride.

A mixture of N-[3-(3-piperidinomethylphenoxy)propyl]ethanediimidamide trihydrochloride (27.3 g; 64.0 mmoles) [prepared in Example 1, Step A], 250 ml of $CH_2Cl_2$ and 26.6 ml (192.0 mmoles) of triethylamine was treated portionwise with N,N'-thiobisphthalimide (DMF solvate) (25.4 g; 64.0 mmoles). After stirring at ambient temperature for one hour, the mixture was washed with 120 ml of 20% KOH, dried (MgSO$_4$), filtered and concentrated, then taken up in 150 ml of toluene and reconcentrated. The product was taken up in 250 ml of 1-propanol and 10.7 ml of 6N HCl, treated with decolorizing carbon and filtered through Celite. This solution was concentrated to 100 ml volume, diluted with 175 ml of dry 1-propanol and stored at 0° C. to give 20.2 g (82.1%) of crystalline hydrochloride salt of the title compound, mp 137°–138° C.

Anal. Calc'd. for $C_{17}H_{25}N_5OS \cdot HCl$: C, 53.18; H, 6.83; N, 18.24; S, 8.35. Found: C, 52.78; H, 6.74; N, 18.52; S, 8.66.

EXAMPLE 11

3-Amino-4-[3-(3-pyrrolidinomethylphenoxy)-propylamino]-1,2,5-thiadiazole

This is a variation of Example 4, Step B, utilizing N,N'-thiobisphthalimide instead of sulfur monochloride.

A mixture of N-[3-(3-pyrrolidinomethylphenoxy)-propyl]ethanediimidamide trihydrochloride (22.0 g; 53.0 mmoles) [prepared in Example 4, Step A],200 ml of $CH_2Cl_2$ and 22 ml of triethylamine was treated with N,N'-thiobisphthalimide (DMF solvate) (21.2 g; 53.0 mmoles). After stirring at ambient temperature for one hour, the mixture was washed with 100 ml of 20% KOH, dried (MgSO$_4$), filtered, diluted with 100 ml of toluene and concentrated. The product was treated with one equivalent of aqueous HCl in 1-propanol to give 13.2 g (67%) of the hydrochloride salt of the title compound, mp 135°–137° C.

Anal. Calc'd. for $C_{16}H_{23}N_5OS \cdot HCl$: C, 51.95; H, 6.54; N, 18.93; S, 8.67. Found: C, 51.92; H, 6.55; N, 19.30; S, 9.06.

EXAMPLE 12

3-Amino-4-{2-[(5-dimethylaminomethyl-3-thienyl)methylthio]-ethylamino}-1,2,5-thiadiazole

A.

N-{2-[(5-dimethylaminomethyl-3-thienyl)methylthio]ethyl}-ethanediimidamide trihydrochloride A suspension of 3-amino-4-{2-[(5-dimethylaminomethyl-3-thienyl)methylthio]ethylamino}-1,2,5-thiadiazole 1-oxide (7.8 g; 22.6 mmoles) [prepared according to published United Kingdom Patent Application No. 2,067,987] in 150 ml of methanol was treated with 15.0 ml of concentrated HCl. After stirring at ambient temperature for 3 hours, the solution was concentrated and the residue triturated with 1-propanol, filtered and dried to give 7.38 g (80%) of product. A sample was recrystallized from methanol-acetone to give the title compound, mp 190°–205° C. (dec.).

Anal. Calc'd. for $C_{12}H_{21}N_5S_2 \cdot 3HCl$: C, 35.25; H, 5.92; N, 17.13. Found: C, 35.03; H, 5.93; N, 17.39.

B.

3-Amino-4-{2-[(5-dimethylaminomethyl-3-thienyl)methylthio]-ethylamino}-1,2,5-thiadiazole A mixture of N-{2-[(5-dimethylaminomethyl-3-thienyl)methylthio]ethyl}ethanediimidamide trihydrochloride (6.13 g; 15.0 mmoles) [prepared in Step A], 60 ml of $CH_2Cl_2$ and 6.3 ml of triethylamine was treated with N,N'-thiobisphthalimide (DMF solvate) (5.96 g; 15.0 mmoles) and stirred for one hour. The mixture was washed with 100 ml of 10% KOH, dried (MgSO$_4$), filtered, diluted with toluene and concentrated to give 5.1 g of product. Treatment of the product with 0.5 molar equivalent of fumaric acid in 1-propanol gave the fumaric acid salt of the compound, mp 141°–143° C. The nmr spectrum in DMSO-d$_6$ shows the presence of approximately 0.12 moles of 1-propanol.

Anal. Calc'd. for $(C_{12}H_{19}N_5S_3)_2 \cdot C_4H_4O_4 \cdot 0.12C_3H_8O$: C, 43.68; H, 5.61; N, 17.75; S, 24.38. Found: C, 43.41; H, 5.53; N, 17.54; S, 24.24.

EXAMPLE 13

3-Amino-4-{2-[(5-piperidinomethyl-3-thienyl)methylthio]ethylamino}-1,2,5-thiadiazole

A.

N-{2-[(5-piperidinomethyl-3-thienyl)methylthio]ethyl-}ethanediimidamide trihydrochloride A suspension of 3-amino-4-{B 2-[(5-piperidinomethyl-3-thienyl)methylthio]ethylamino}-1,2,5-thiadiazole 1-oxide (6.1 g; 15.8 mmoles) [prepared according to published United Kingdom Patent Application No. 2,067,987] in 80 ml of methanol was treated with 10.5 ml of concentrated HCl. After stirring at ambient temperature for 3 hours, the solution was concentrated and the residue triturated with 50 ml of 1-propanol, filtered and dried to give 5.86 g (83%) of product. A sample was recrystallized from methanol-acetone to give the title compound, mp 201°–214° C. (dec.).

Anal. Calc'd. for $C_{15}H_{25}N_5S_2\cdot 3HCl$: C, 40.13; H, 6.29; N, 15.60; S, 14.29. Found: C, 39.97; H, 6.47; N, 15.28; S, 14.63.

B.

3-Amino-4-{2-[(5-piperidinomethyl-3-thienyl)methylthio]-ethylamino}-1,2,5-thiadiazole A mixture of N-{2-[(5-piperidinomethyl-3-thienyl)methylthio]ethyl}ethanediimidamide trihydrochloride (5.17 g; 11.5 mmoles) [prepared in Step A], 48 ml of $CH_2Cl_2$ and 4.8 ml of triethylamine was treated with N,N'-thiobisphthalimide (DMF solvate) (4.57 g; 11.5 mmoles) and stirred for one hour. The mixture was washed with 90 ml of 10% KOH, dried (MgSO$_4$), filtered, diluted with toluene and concentrated to give 4.5 g of product. Treatment of the product with one equivalent of cyclohexyl sulfamic acid in methanol gave the cyclohexyl sulfamate salt of the title compound, mp 142°–143° C.

Anal. Calc'd. for $C_{15}H_{23}N_5S_3\cdot C_6H_{13}NO_3S$: C, 45.96; H, 6.61; N, 15.31; S, 23.38. Found: C, 45.61; H, 6.41; N, 15.46; S, 23.48.

EXAMPLE 14

The general procedures of Example 1, Step A, and then either Example 1, Step B, or Example 10 is repeated except that the 3-amino-4-[3-(3-piperidinomethylphenoxy)propylamino]-1,2,5-thiadiazole 1-oxide utilized therein is replaced by an equimolar amount of (a)  3-ethylamino-4-[3-(3-piperidinomethylphenoxy)-propylamino]-1,2,5-thiadiazole 1-oxide,
(b)  3-allylamino-4-[3-(3-piperidinomethylphenoxy)propylamino]-1,2,5-thiadiazole 1-oxide,
(c)  3-(2-propynyl)-4-[3-(3-piperidinomethylphenoxy)propylamino]-1,2,5-thiadiazole 1-oxide,
(d) 3-(3-pyridylmethylamino)-4-[3-(3-piperidinomethylphenoxy)propylamino]-1,2,5-thiadiazole 1-oxide,
(e)  3-(6-methyl-3-pyridyl)methylamino-4-[3-(3-piperidinomethylphenoxy)propylamino]-1,2,5-thiadiazole 1-oxide and
(f)  3-(3,4-methylenedioxybenzylamino)-4-[3-(3-piperidinomethylphenoxy)propylamino]-1,2,5-thiadiazole 1-oxide, respectively, and there is thereby produced (a)  3-ethylamino-4-[3-(3-piperidinomethylphenoxy)-propylamino]-1,2,5-thiadiazole,
(b)  3-allylamino-4-[3-(3-piperidinomethylphenoxy)propylamino]-1,2,5-thiadiazole,
(c)  3-(2-propynyl)-4-[3-(3-piperidinomethylphenoxy)propylamino]-1,2,5-thiadiazole,
(d) 3-(3-pyridylmethylamino)-4-[3-(3-piperidinomethylphenoxy)propylamino]-1,2,5-thiadiazole,
(e)  3-(6-methyl-3-pyridyl)methylamino-4-[3-(3-piperidinomethylphenoxy)propylamino]-1,2,5-thiadiazole and
(f)  3-(3,4-methylenedioxybenzylamino)-4-[3-(3-piperidinomethylphenoxy)propylamino]-1,2,5-thiadiazole, respectively.

EXAMPLE 15

3-Amino-4-[3-(6-piperidinomethyl-2-pyridyloxy)-propylamino]-1,2,5-thiadiazole

A.

3-Amino-4-[3-(6-piperidinomethyl-2-pyridyloxy)-propylamino]-1,2,5-thiadiazole 1-oxide A solution of 3-(6-piperidinomethyl-2-pyridyloxy)propylamine (4.65 g; 18.6 mmoles) [prepared according to published United Kingdom Patent Application No. 2,098,988] in 50 ml of methanol was reacted with 3-amino-4-methoxy-1,2,5-thiadiazole 1-oxide (2.74 g; 18.6 mmoles) according to the general procedure described in United Kingdom Patent Application No. 2,067,987 to give a solution containing 3-amino-4-[3-(6-piperidinomethyl-2-pyridyloxy)propylamino]-1,2,5-thiadiazole 1-oxide. A purified sample melted at 145°–147° C.

B.

N-[3-(6-Piperidinomethyl-2-pyridyloxy)propyl]ethanediimidamide trihydrochloride A methanolic solution of the product prepared in Step A was diluted to 100 ml and 12.4 ml of concentrated HCl was added. The solution was stirred at ambient temperature for 18 hours, concentrated, and the residue was dissolved in 80 ml of water and extracted twice with $CH_2Cl_2$. The aqueous layer was concentrated, treated with n-propanol and concentrated under high vacuum to give the title compound as a foam.

C.

3-Amino-4-[3-(6-piperidinomethyl-2-pyridyloxy)-propylamino]-1,2,5-thiadiazole A mixture of the crude product prepared in Step B in 80 ml of $CH_2Cl_2$ and containing 7.69 ml of triethylamine was treated with N,N'-thiobisphthalimide (DMF solvate) (7.35 g; 18.5 mmoles). After stirring at ambient temperature for one hour, the mixture was washed with 50 ml of 4N NaOH, water, saturated aqueous NaCl solution, dried (Na$_2$SO$_4$), filtered and evaporated under reduced pressure to give the crude product. The product was purified by flash chromatography on 100 g of silica gel (230–400 mesh) using ethyl acetate-methanol (95:5) as the eluent to give 3.63 g of the title compound as a viscous oil. Treatment of the product with one equivalent of cyclohexyl sulfamic acid in acetone gave the cyclohexyl sulfamate salt of the title compound, mp 125.5°–131° C.

Anal. Calc'd. for $C_{16}H_{24}N_6OS\ C_6H_{13}NO_3S$: C, 50.07; H, 7.07; N, 18.58; S, 12.15. Found: C, 50.02; H, 7.03; N, 18.54; S, 12.14.

EXAMPLE 16

3-Amino-4-[3-(6-dimethylaminomethyl-2-pyridyloxy)-propylamino]-1,2,5-thiadiazole When a methanolic solution of 3-(6-dimethylaminomethyl-2-pyridyloxy)propylamine [prepared according to published United Kingdom Patent Application No. 2,098,988] is reacted with 3-amino-4-methoxy-1,2,5-thiadiazole 1-oxide according to the general procedure described in United Kingdom Patent Application No. 2,067,987 and the resulting 3-amino-4-[3-(6-piperidinomethyl-2-pyridyloxy)propylamino]-1,2,5-thiadiazole 1-oxide is successively reacted by the general procedure described in Example 1, Step A, and then by either Example 1, Step B, or Example 10, the title compound is thereby produced.

EXAMPLE 17

3-Amino-4-{2-[(6-dimethylaminomethyl-2-pyridyl)methylthio]ethylamino}-1,2,5-thiadiazole When a suspension of 3-amino-4-{2-[(6-dimethylaminomethyl-2-pyridyl)methylthio]ethylamino}-1,2,5-thiadiazole 1-oxide [prepared according to published United Kingdom Patent Application No. 2,067,987] is successively reacted according to the procedures of Example 1, Step A, and then by either Example 1, Step B, or Example 10, the title compound is thereby produced.

EXAMPLE 18

3-Amino-4-{2-[(6-piperidinomethyl-2-pyridyl)methylthio]ethylamino}-1,2,5-thiadiazole When a suspension of 3-amino-4-{2-[(6-piperidinomethyl-2-pyridyl)methylthio]ethylamino}-1,2,5-thiadiazole 1-oxide [prepared according to published United Kingdom Patent Application No. 2,067,987] is successively reacted according to the procedures of Example 1, Step A, and then by either Example 1, Step B, or Example 10, the title compound is thereby produced.

EXAMPLE 19

The general procedure of Example 1, Step A, and then either Example 1, Step B, or Example 10 is repeated except that the 3-amino-4-[3-(3-piperidinomethylphenoxy)propylamino]-1,2,5-thiadiazole 1-oxide utilized therein is replaced by an equimolar amount of
(a) 3-amino-4-[3-(3-piperidinomethylthiophenoxy)propylamino]-1,2,5-thiadiazole 1-oxide,
(b) 3-amino-4-[3-(3-dimethylaminomethylthiophenoxy)propylamino]-1,2,5-thiadiazole 1-oxide,
(c) 3-amino-4-[3-(3-pyrrolidinomethylthiophenoxy)propylamino]-1,2,5-thiadiazole 1-oxide,
(d) 3-amino-4-[3-(4-dimethylaminomethyl-2-pyridyloxy)propylamino]-1,2,5-thiadiazole 1-oxide,
(e) 3-amino-4-[3-(5-dimethylaminomethyl-3-thienyloxy)propylamino]-1,2,5-thiadiazole 1-oxide,
(f) 3-amino-4-[3-(5-piperidinomethyl-3-thienyloxy)propylamino]-1,2,5-thiadiazole 1-oxide,
(g) 3-amino-4-{2-[(4-dimethylaminomethyl-2-pyridyl)methylthio]ethylamino}-1,2,5-thiadiazole 1-oxide and
(h) 3-amino-4-{2-[(4-piperidinomethyl-2-pyridyl)methylthio]ethylamino}-1,2,5-thiadiazole 1-oxide, respectively,
and there is thereby produced (a) 3-amino-4-[3-(3-piperidinomethylthiophenoxy)propylamino]-1,2,5-thiadiazole,
(b) 3-amino-4-[3-(3-dimethylaminomethylthiophenoxy)propylamino]-1,2,5-thiadiazole,
(c) 3-amino-4-[3-(3-pyrrolidinomethylthiophenoxy)propylamino]-1,2,5-thiadiazole,
(d) 3-amino-4-[3-(4-dimethylaminomethyl-2-pyridyloxy)propylamino]-1,2,5-thiadiazole,
(e) 3-amino-4-[3-(5-dimethylaminomethyl-3-thienyloxy)propylamino]-1,2,5-thiadiazole,
(f) 3-amino-4-[3-(5-piperidinomethyl-3-thienyloxy)propylamino]-1,2,5-thiadiazole,
(g) 3-amino-4-{2-[(4-dimethylaminomethyl-2-pyridyl)methylthio]ethylamino}-1,2,5-thiadiazole and
(h) 3-amino-4-{2-[(4-piperidinomethyl-2-pyridyl)methylthio]ethylamino}-1,2,5-thiadiazole, respectively.

The above starting materials are prepared according to the general procedures described in published U.K. Patent Application No. 2,067,987. The precursors of the starting materials are prepared by the procedures and analogous general procedures described in U.K. Patent Application Nos. 2,067,987, 2,098,988, 2,063,875 and published European Patent Application No. 49,173.

EXAMPLE 20

3-Amino-4-[3-(4-piperidinomethyl-2-pyridyloxy)propylamino]-1,2,5-thiadiazole

A. 3-(4-Piperidinomethyl-2-pyridyloxy)propylamine

When the general procedure for the preparation of 3-(6-piperidinomethyl-2-pyridyloxy)propylamine described in U.K. Patent Application No. 2,098,988 was followed except that the 2-chloro-6-methylpyridine utilized therein was replaced by 2-bromo-4-methylpyridine, then the title compound was produced as an oil.

Anal. Calc'd. for $C_{14}H_{23}N_3O$: C, 67.44; H, 9.30; N, 16.85. Found: C, 67.54; H, 8.98; N, 16.55.

B.

3-Amino-4-[3-(4-piperidinomethyl-2-pyridyloxy)propylamino]-1,2,5-thiadiazole 1-oxide A solution of the product of Step A (6.5 g; 26.0 mmoles) in 90 ml of methanol was reacted with 3-amino-4-methoxy-1,2,5-thiadiazole 1-oxide (3.84 g; 26.0 mmoles) according to the general procedures described in U.K. Patent Application No. 2,067,987 to give 6.33 g of product. Recrystallization from methanol-acetonitrile yielded the title compound, mp 154°–158° C.

Anal. Calc'd. for $C_{16}H_{24}N_6OS$: C, 52.73; H, 6.64; N, 23.06; S, 8.80. Found: C, 52.72; H, 6.30; N, 23.32; S, 8.74.

C.

N-[3-(4-Piperidinomethyl-2-pyridyloxy)propyl]ethanediimidamide trihydrochloride

The product of Step B (5.0 g; 13.7 mmoles) was dissolved in 80 ml of methanol and treated with 9.1 ml of concentrated HCl. After stirring at ambient temperature for 4.5 hours, the solution was evaporated to dryness under reduced pressure to give the title compound.

D.

3-Amino-4-[3-(4-piperidinomethyl-2-pyridyloxy)propylamino]-1,2,5-thiadiazole

A mixture of the product prepared in Step C in 50 ml of $CH_2Cl_2$ and 5.7 ml of triethylamine was treated with N,N'-thiobisphthalimide (DMF solvate) (5.44 g; 13.7 mmoles). After stirring at ambient temperature for one hour, the mixture was washed with 40 ml of 4N NaOH, water, saturated aqueous NaCl solution, dried (Na$_2$SO$_4$), filtered and evaporated under reduced pressure to give the crude product. The product was purified by flash chromatography on 90 g of silica gel (230–400 mesh) using ethyl acetate-methanol (96:4) as the eluent to give 3.44 g of the title compound as a viscous oil. Treatment of the product with one equivalent of cyclohexyl sulfamic acid in acetone gave the cyclohexyl sulfamate of the title compound, mp 1245.5°–126° C.

Anal. Calc'd. for C$_{16}$H$_{24}$N$_6$OS·C$_6$H$_{13}$NO$_3$S: C, 50.07; H, 7.07; N, 18.58; S, 12.15. Found: C, 50.47; H, 7.12; N, 18.33; S, 11.87.

EXAMPLE 21

3-Amino-4-{3-[3-(1,2,3,6-tetrahydro-1-pyridyl)methylphenoxy]propylamino}-1,2,5-thiadiazole The general procedure of Example 15 was repeated, except that the 3-(6-piperidinomethyl-2-pyridyloxy)propylamine utilized therein was replaced by an equivalent amount of 3-[3-(1,2,3,6-tetrahydro-1-pyridyl)methylphenoxy]propylamine, to give 2.31 g of product. Crystallization from toluene yielded the title compound, mp 99.5°–104° C.

Anal. Calc'd. for C$_{17}$N$_{23}$N$_5$OS: C, 59.10; H, 6.71; N, 20.27; S, 9.28. Found (corr. for 2.19% H$_2$O): C, 58.78; H, 6.71; N, 19.90; S, 9.26.

We claim:

1. A compound of the formula

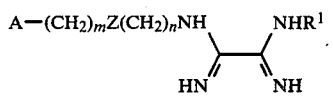

wherein R$^1$ is hydrogen, (lower)alkyl, 2-fluoroethyl, 2,2,2-trifluoroethyl, allyl, propargyl,

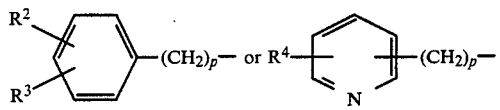

in which p is 1 or 2, R$^2$ and R$^3$ each are independently hydrogen, (lower)alkyl, (lower)alkoxy or halogen, and, when R$^2$ is hydrogen, R$^3$ also may be trifluoromethyl, or R$^2$ and R$^3$, taken together, may be methylenedioxy, and R$^4$ is hydrogen, (lower)alkyl or (lower)alkoxy;

m is an integer of from 0 to 2 inclusive;

n is an integer of from 2 to 5 inclusive;

Z is oxygen, sulfur or methylene; and

A is

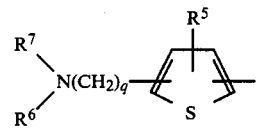

in which R$^5$ is hydrogen, (lower)alkyl or (lower)alkoxy, q is an integer of from 1 to 4 inclusive and R$^6$ and R$^7$ each are independently (lower)alkyl, (lower)alkoxy (lower)alkyl in which the (lower)alkoxy moiety is at least two carbon atoms removed from the nitrogen atom, or phenyl(lower)alkyl, and, when R$^6$ is hydrogen, R$^7$ also may be cyclo(lower)alkyl, or R$^6$ and R$^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, N-methylpiperazino, 1,2,3,6-tetrahydropyridyl, homopiperidino, heptamethyleneimino, octamethyleneimino, 3-azabicyclo[3.2.2]non-3-yl or 3-pyrrolino; or a salt, hydrate or solvate thereof.

2. A compound of claim 1 having the formula

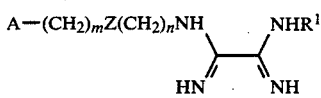

wherein R$^1$ is hydrogen or (lower)alkyl, m is 0 or 1, n is 2 or 3, Z is oxygen or sulfur and A is

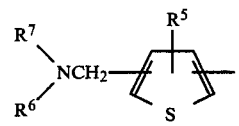

in which R$^5$ is hydrogen or methyl, and R$^6$ and R$^7$ each are independently methyl or ethyl, or when taken together with the nitrogen to which they are attached, R$^6$ and R$^7$ represent a pyrrolidino or piperidino ring; or a salt, hydrate or solvate thereof.

3. A compound of claim 1 having the formula

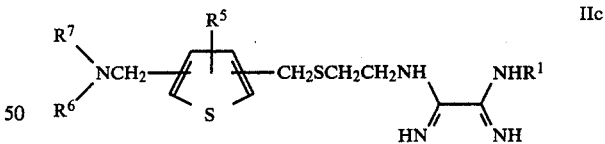

wherein R$^1$ and R$^5$ each are independently hydrogen or methyl, and R$^6$ and R$^7$ each are independently methyl or ethyl; or a salt, hydrate or solvate thereof.

4. The compound of claim 1 which is N-{2-[(5-dimethylaminomethyl-4-methyl-2-thienyl)methylthio]ethyl}ethanediimidamide, or a salt, hydrate or solvate thereof.

5. The compound of claim 1 which is N-{2-[(5-dimethylaminomethyl-3-thienyl)methylthio]ethyl}ethanediimidamide, or a salt, hydrate or solvate thereof.

6. The compound of claim 1 which is N-{2-[(5-piperidinomethyl-3-thienyl)methylthio]ethyl}ethanediimidamide, or a salt, hydrate or solvate thereof.

* * * * *